(12) United States Patent
Dolecek et al.

(10) Patent No.: US 9,028,388 B2
(45) Date of Patent: May 12, 2015

(54) MULTI-UNIT BLOOD PROCESSOR WITH VOLUME PREDICTION

(75) Inventors: Victor D. Dolecek, Englewood, CO (US); Darryl Hudock, Highlands Ranch, CO (US)

(73) Assignee: Terumo BCT, Inc., Lakewood, CO (US)

( * ) Notice: Subject to any disclaimer, the term of this patent is extended or adjusted under 35 U.S.C. 154(b) by 1013 days.

(21) Appl. No.: 13/102,728

(22) Filed: May 6, 2011

(65) Prior Publication Data

US 2011/0301012 A1    Dec. 8, 2011

Related U.S. Application Data

(60) Provisional application No. 61/352,106, filed on Jun. 7, 2010.

(51) Int. Cl.
| | | |
|---|---|---|
| *B04B 5/04* | (2006.01) | |
| *B04B 11/00* | (2006.01) | |
| *A61M 1/36* | (2006.01) | |
| *B04B 13/00* | (2006.01) | |

(52) U.S. Cl.
CPC .............. *B04B 5/0428* (2013.01); *B04B 11/00* (2013.01); *A61M 1/3693* (2013.01); *A61M 2205/3331* (2013.01); *A61M 2205/3379* (2013.01); *B04B 5/0442* (2013.01); *B04B 2013/006* (2013.01); *A61M 1/3696* (2014.02); *A61M 1/3698* (2014.02)

(58) Field of Classification Search
CPC .... B04B 5/0407; B04B 5/0428; B04B 11/04; B04B 13/00; B04B 2013/006
USPC ...................... 494/10, 37, 45; 604/6.01–6.06; 210/782, 787, 789
See application file for complete search history.

(56) References Cited

U.S. PATENT DOCUMENTS

| | | |
|---|---|---|
| 3,297,244 A | 1/1967 | Hein |
| 3,326,458 A | 6/1967 | Merman et al. |
| 3,679,128 A | 7/1972 | Unger et al. |
| 3,708,110 A | 1/1973 | Unger et al. |
| 3,718,133 A | 2/1973 | Perry et al. |
| 3,724,747 A | 4/1973 | Unger et al. |
| 3,737,096 A | 6/1973 | Jones et al. |
| 3,747,843 A | 7/1973 | Joyce |
| 3,858,796 A | 1/1975 | Unger et al. |
| 3,921,898 A | 11/1975 | Finkel |

(Continued)

FOREIGN PATENT DOCUMENTS

| | | |
|---|---|---|
| DE | 20015684 U1 | 2/2001 |
| EP | 0014093 B1 | 5/1983 |

(Continued)

OTHER PUBLICATIONS

PCT/US2011/035556, "International Search Report", mailed Nov. 19, 2011.

(Continued)

*Primary Examiner* — Timothy Cleveland
(74) *Attorney, Agent, or Firm* — René A. Pereyra

(57) ABSTRACT

Method and Apparatus for predicting the volume of a component separated from a composite fluid by predicting the volume of the composite fluid from sensed pressure and predicting the volume of other separated components from sensed movement of the other components to collection bags.

16 Claims, 3 Drawing Sheets

(56) References Cited

U.S. PATENT DOCUMENTS

| | | |
|---|---|---|
| 3,987,961 A | 10/1976 | Sinn et al. |
| 4,091,989 A | 5/1978 | Schlutz |
| 4,098,456 A | 7/1978 | Bayham |
| 4,146,172 A | 3/1979 | Cullis et al. |
| 4,296,882 A | 10/1981 | Kobayashi |
| 4,303,193 A | 12/1981 | Latham, Jr. |
| 4,389,207 A | 6/1983 | Bacehowski et al. |
| 4,405,079 A | 9/1983 | Schoendorfer |
| 4,421,503 A | 12/1983 | Latham, Jr. et al. |
| 4,482,342 A | 11/1984 | Lueptow et al. |
| 4,720,284 A | 1/1988 | McCarty |
| 4,767,397 A | 8/1988 | Hohenberg et al. |
| 4,781,687 A | 11/1988 | Wall |
| 4,842,576 A | 6/1989 | Lysaght et al. |
| 4,850,952 A | 7/1989 | Figdor et al. |
| 4,850,995 A | 7/1989 | Tie et al. |
| 4,887,411 A | 12/1989 | Rondeau et al. |
| 4,911,703 A | 3/1990 | Lysaght et al. |
| 4,939,081 A | 7/1990 | Figdor et al. |
| 4,990,132 A | 2/1991 | Unger et al. |
| 5,114,396 A | 5/1992 | Unger et al. |
| 5,427,695 A | 6/1995 | Brown |
| 5,632,906 A | 5/1997 | Ishida et al. |
| 5,637,082 A | 6/1997 | Pages et al. |
| 5,651,766 A | 7/1997 | Kingsley et al. |
| 5,723,050 A | 3/1998 | Unger et al. |
| 5,728,060 A | 3/1998 | Kingsley et al. |
| 5,733,253 A | 3/1998 | Headley et al. |
| 5,738,644 A | 4/1998 | Holmes |
| 5,770,069 A | 6/1998 | Meryman |
| 5,779,660 A | 7/1998 | Kingsley et al. |
| 5,853,382 A | 12/1998 | Kingsley et al. |
| 5,874,208 A | 2/1999 | Unger |
| 5,885,239 A | 3/1999 | Headley et al. |
| 5,904,355 A | 5/1999 | Powers et al. |
| 5,964,724 A | 10/1999 | Rivera et al. |
| 6,007,509 A | 12/1999 | Kingsley et al. |
| 6,019,742 A | 2/2000 | Headley et al. |
| 6,027,441 A | 2/2000 | Cantu et al. |
| 6,039,711 A | 3/2000 | Headley et al. |
| 6,060,022 A | 5/2000 | Pang et al. |
| 6,074,335 A | 6/2000 | Headley et al. |
| 6,099,491 A | 8/2000 | Headley et al. |
| 6,102,883 A | 8/2000 | Kingsley et al. |
| 6,254,784 B1 | 7/2001 | Nayak et al. |
| 6,261,217 B1 | 7/2001 | Unger et al. |
| 6,296,602 B1 | 10/2001 | Headley |
| 6,315,706 B1 | 11/2001 | Unger et al. |
| 6,348,031 B1 | 2/2002 | Unger et al. |
| 6,348,156 B1 | 2/2002 | Vishnoi et al. |
| 6,413,200 B1 | 7/2002 | Jorgensen et al. |
| 6,524,231 B1 | 2/2003 | Westberg et al. |
| 6,582,349 B1 | 6/2003 | Cantu et al. |
| 6,585,499 B2 | 7/2003 | Nguyen et al. |
| 6,602,179 B1 | 8/2003 | Headley et al. |
| 6,605,223 B2 | 8/2003 | Jorgensen et al. |
| 6,652,475 B1 | 11/2003 | Sahines et al. |
| 6,656,105 B2 | 12/2003 | Hogberg et al. |
| 6,666,665 B1 | 12/2003 | Nguyen et al. |
| 6,733,433 B1 | 5/2004 | Fell |
| 6,740,239 B2 | 5/2004 | Hogberg et al. |
| 6,827,863 B2 | 12/2004 | Dolecek et al. |
| 6,852,074 B1 | 2/2005 | Jorgenson et al. |
| 7,033,512 B2 | 4/2006 | Hlavinka et al. |
| 7,166,217 B2 | 1/2007 | Holmes et al. |
| 7,241,281 B2 | 7/2007 | Coelho et al. |
| 7,279,107 B2 | 10/2007 | Hogberg et al. |
| 7,347,932 B2 | 3/2008 | Holmes et al. |
| 7,413,665 B2 | 8/2008 | Holmes et al. |
| 7,425,192 B2 | 9/2008 | Sacco et al. |
| 7,442,178 B2 | 10/2008 | Chammas |
| 7,497,944 B2 | 3/2009 | Hogberg et al. |
| 7,674,221 B2 | 3/2010 | Hudock et al. |
| 7,766,809 B2 | 8/2010 | Dolecek et al. |
| 7,819,793 B2 | 10/2010 | Lindell et al. |
| 2008/0053203 A1 | 3/2008 | Hogberg et al. |
| 2008/0147240 A1 | 6/2008 | Hudock et al. |
| 2008/0220959 A1 | 9/2008 | Holmes et al. |
| 2009/0317305 A1 | 12/2009 | Hudock et al. |
| 2010/0026986 A1 | 2/2010 | Stanton et al. |
| 2010/0273627 A1 | 10/2010 | Hudock et al. |

FOREIGN PATENT DOCUMENTS

| | | |
|---|---|---|
| EP | 0350495 B1 | 8/1992 |
| EP | 0536594 A1 | 4/1993 |
| EP | 0235160 B1 | 6/1994 |
| EP | 0771569 B1 | 5/1997 |
| EP | 0578086 B1 | 8/2001 |
| EP | 1208856 A2 | 5/2002 |
| EP | 0791367 B1 | 8/2005 |
| EP | 1566191 A2 | 8/2005 |
| WO | 92/00145 A1 | 1/1992 |
| WO | 00/54823 A1 | 9/2000 |
| WO | 00/54824 A1 | 9/2000 |
| WO | 01/02037 A1 | 1/2001 |
| WO | 03/089027 A2 | 10/2003 |
| WO | 2004/018021 A2 | 3/2004 |

OTHER PUBLICATIONS

EP 06076187.1-2310: Extended European Search Report, Oct. 19, 2006.
EP 06076188.9: European Search Report, Nov. 3, 2006.
EP 06076188.9: Extended European Search Report, Feb. 14, 2007.
PCT/US06/21827: International Search Report and Written Opinion, Oct. 20, 2006.
PCT/US06/21674: International Search Report and Written Opinion, Oct. 20, 2006.
PCT/US07/076987: International Search Report, Apr. 23, 2008.

MULTI-UNIT BLOOD PROCESSOR WITH VOLUME PREDICTION

CROSS REFERENCE TO RELATED APPLICATIONS

This application claims the benefit of U.S. Provisional Application No. 61/352,106 filed Jun. 7, 2010.

FIELD OF THE INVENTION

The present invention relates to apparatus and method for separating at least two discrete volumes of blood into at least two components each.

Background

U.S. application Ser. No. 11/954,388 filed Dec. 12, 2007 describes an apparatus for separating discrete volumes of a composite liquid such as blood into at least two components.

The apparatus and method of this application relate to the separation of biological fluids comprising an aqueous component and one or more cellular components. Examples given include: extracting a plasma component and a cellular component (including platelets, white blood cells, and red blood cells) from a volume of whole blood. A component, such as washed red blood cells, may also be filtered so as to remove residual prions, white blood cells or platelets from the red blood cells.

An apparatus for processing blood components that can process at once at least two discrete volumes of a composite liquid, in particular, two unequal volumes wherein the proportions of the various components of the composite liquid that may vary from one discrete volume to another one, is known from U.S. application Ser. No. 11/954,388. A method is described therein for separating at least two discrete volumes of a composite liquid into at least a first component and a second component. The method comprises at least two separation bags containing two discrete volumes of a composite liquid in separation cells mounted on a rotor; storing in at least one container on the rotor at least two first component bags connected to the at least two separation bags respectively; separating at least a first and a second components in each of the separation bags; transferring at least one fraction of a first separated component into a component bag; detecting a characteristic of a component at a location in each separation bag; and stopping transferring the fraction of the first component upon detection of the characteristic of a component at the first determined location.

SUMMARY OF THE INVENTION

The present invention comprises improvements on a centrifugal blood separation device capable of processing a plurality of blood units at the same time.

The invention includes a method of predicting the volume of a component separated from a composite fluid comprising loading a composite fluid into a separation cavity on a centrifuge, sensing the fluid pressure in the separation cavity after the loading step, predicting the volume of the composite fluid from the sensing the fluid pressure step, separating the composite fluid into at least a first and second component, expressing the first separated component from the separation cavity to a collection cavity, sensing the movement of the first separated component, determining the volume of the expressed separated component from the sensing the movement step and predicting the volume of the second component remaining in the separation cavity from the determined volume of the composite fluid and the predicted volume of the expressed first component.

The method further may comprise sensing, optically with a photocell, the leading edge of the expressed first component by detecting the presence of fluid in the tubing between the separation cavity and the collection cavity and sensing, optically with a photocell located near the exit of the separation cavity, the trailing edge of the expressed first component by detecting the presence of components not in the first expressed component.

The invention further may include separating the composite fluid into at least a first, second and third component; expressing the third separated component from the separation cavity to a collection cavity after the step of expressing the first separated component, sensing the movement of the third separated component, determining the volume of the expressed third separated component from the sensing the movement step, predicting the volume of the second component remaining in the separation cavity from the predicted volume of the composite fluid, the determined volume of the expressed first component and the predicted volume of the expressed third component. The composite fluid can also be whole blood, the first component plasma, the third component platelets and the second component red blood cells. The method may further include centrifugally separating the composite fluid. The expressing step can comprise squeezing the separation bag to transfer the first and the third components to respective collection bags.

The method may further comprise sensing the movement of the plasma which may comprise sensing the leading edge of the plasma by detecting the presence of the plasma, and sensing the trailing edge of the plasma by detecting the presence of platelets. Sensing the movement of the platelets may comprise sensing the leading edge of the platelets by detecting the presence of the platelets and sensing the trailing edge of the platelets by detecting the presence of red blood cells. Sensing the movement of the plasma may comprise sensing the leading edge of the plasma by detecting the presence of the plasma and sensing the trailing edge of the plasma by detecting the presence of a cellular component.

The invention also may include apparatus for predicting the volume of a separated component, the apparatus comprising a rotor having at least one separation cavity and at least one collection cavity for centrifugally separating the composite fluid, which may be whole blood, into a first separated component, which may be plasma, a second separated component, which may be red blood cells, and an optional third separated component, which may be a platelet component; a separation bag containing a composite fluid in the separation cavity; at least one collection bag in the collection cavity; tubing connecting the separation bag to the at least one collection bag; a pressure sensor for detecting a pressure amount due to the composite fluid in the separation bag; a first sensor for detecting components in the tubing; a second sensor for detecting changes in separated components in the separation bag; and a controller for predicting the volume of the composite fluid from the amount of pressure sensed by the pressure sensor, determining the volume of any separated component passing from the separation bag through the tubing to the collection bag from detection by the first and second sensors, and predicting the volume of any separated component remaining in the separation bag from the volume prediction of the composite fluid and the volume determination of the separated component passing from the separation bag to the collection bag.

The apparatus of the invention additionally may use a squeezing system for squeezing the separation bag to transfer separated components to the collection bag. This squeezing system squeezes the separation bag to transfer separated components to the collection bag, wherein the plasma component is transferred from the separation bag to a plasma collection bag and the platelet component is transferred from the separation bag to a platelet collection bag.

The apparatus also may comprise a pressure sensor, located on the wall of the separation cavity, that detects a pressure amount due to the fluid level of the composite fluid in the separation bag. In addition a first optical sensor may detect the leading edge of the first separated component and is located to detect fluid in a tube. A second optical sensor, located on a wall of the separation cavity, may detect the trailing edge of a separated component by detecting another component.

Other features and advantages of the invention will appear from the following description and accompanying drawings, which are to be considered exemplary only.

DESCRIPTION OF EMBODIMENT

For the sake of clarity, the invention will be described with respect to a specific use, namely the separation of whole blood into at least two components, in particular into a plasma component and a red blood cell component, or into a plasma component, a platelet component and a red blood cell component. The discrete volume mentioned hereunder will typically be the volume of a blood donation. The volume of a blood donation may vary from one donor to another one (for example, 500 ml plus or minus 10% in the United States). Also, the proportion of the components of blood usually varies from one donor to another one. It should be understood however that this specific use is exemplary only.

It is understood that white blood cells could further be separated and collected with suitable volume predictions in accordance with this invention. Thus the invention may further be used to collect plasma, platelets, white blood cells and red blood cells for a four component collection.

Figure 1:
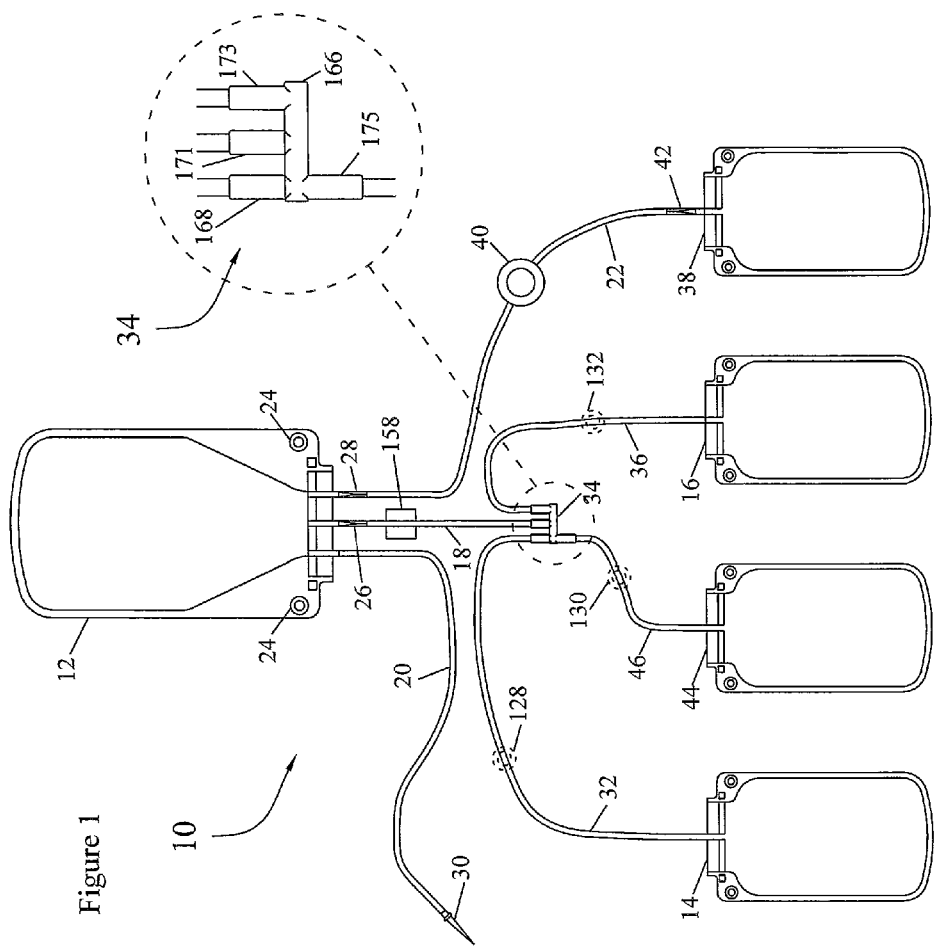
FIG. 1 is a schematic view of a first set of bags designed for cooperating with a separation apparatus.

FIG. 1 shows an example of a set 10 of bags adapted to be used for the separation of a composite liquid (e.g. whole blood) into at least one component (e.g. plasma, platelets, or both) and a second component (e.g. red blood cells). This bag set comprises a flexible primary separation bag 12 and flexible component or satellite bags 14, 16, 38 and 44 connected thereto.

The bag 10 is shown with an asymmetrical manifold 34 forming an E shape as more fully described below. The manifold 34 is representative in shape in that it is understood that other configurations with varying number of arms or connectors could be used depending on specific use of the apparatus, (namely the separation of whole blood into at least two components, in particular into a plasma component and a red blood cell component, or into a plasma component, a platelet component and a red blood cell component or with a washing feature or white blood cell collection.

When the composite liquid is whole blood, the separation bag 12 has two purposes, and is successively used as a collection bag and as a separation bag. It is intended to initially receive a discrete volume of whole blood from a donor (usually about 500 ml but can vary as described above) and to be used later as a separation chamber in a separation apparatus. The separation bag 12 is flat and generally rectangular. It is made of two sheets of plastic material that are welded together so as to define there between an interior space having a main rectangular portion connected to a triangular proximal portion. A first tube 18 is connected to a proximal end of the triangular portion, and a second tube 20 and a third tube 22 are connected on opposite sides adjacent the first tube 18. The proximal ends of the three tubes 18, 20, 22 are embedded between the two sheets of plastic material so as to be parallel. The separation bag 12 further, optionally, comprises a hole 24 in each of its two proximal corners that are adjacent to the three tubes 18, 20, 22. The holes 24 may be used to optionally secure the separation bag to a separation cell on a centrifugal blood separation apparatus.

The separation bag 12 initially contains a volume of anti-coagulant solution (typically about 63 ml of a solution of citrate phosphate dextrose for a blood donation of about 450 ml). The first and third tubes 18, 22 are fitted at their proximal ends with a breakable stopper 26, 28 respectively, blocking liquid flow therethrough. The breakable stopper is sometimes called a "frangible". The second tube 20 is a collection tube having a needle 30 connected to its distal end. At the beginning of a blood donation, the needle 30 is inserted in the vein of a donor and blood flows into the separation bag 12. After a desired volume of blood has been collected in the separation bag 12, the collection tube 20 is sealed and cut, disconnecting the needle from the bag set 10. Alternatively, previously collected blood may be transferred to the separation bag 12 through the collection tube 20, with or without the use of the needle 30.

The first component bag 14 is intended for receiving a plasma component. The bag 14 is flat and substantially rectangular. It is connected through a plasma collection tube 32 and an asymmetric manifold 34 to the first tube 18. The second component bag 16 is intended for receiving a platelet component. The second component bag 16 is also flat and substantially rectangular. It is connected through a platelet collection tube 36 and the asymmetric manifold 34 to the first tube 18. A third component bag 38 is intended to receive a red blood cell component (which may be washed), from the primary bag 12. Red blood cells may be drained through tube 22, which may include a filter 40, into third component bag 38. A breakable stopper 42 or frangible in tube 22 as well as frangible 28 prevents premature flow of red blood cells into the third component bag 38.

An optional wash solution bag 44, if used, may initially contain wash solution such as saline or the bag 44 may contain storage solution such as SAGM if no washing is desired. Wash solution may be transferred through a wash solution tube 46 and the asymmetrical manifold 34 by way of the first tube 18 into the primary bag 12 when the primary bag 12 contains high hematocrit blood cells. "High hematocrit" means a percentage of red blood cell volume to total fluid volume of at least 80 percent, more preferably 90 percent, and yet more preferably 95 percent. After wash solution is mixed with high hematocrit red blood cells and subsequently separated, used wash solution may be extracted through the first tube 18, asymmetrical manifold 34, and discard tube 46 into a wash solution discard bag 44. The discard bag 44 could also be used to collect a blood component, such as for example, mesenchymal stem cells or white blood cells.

Figure 2:
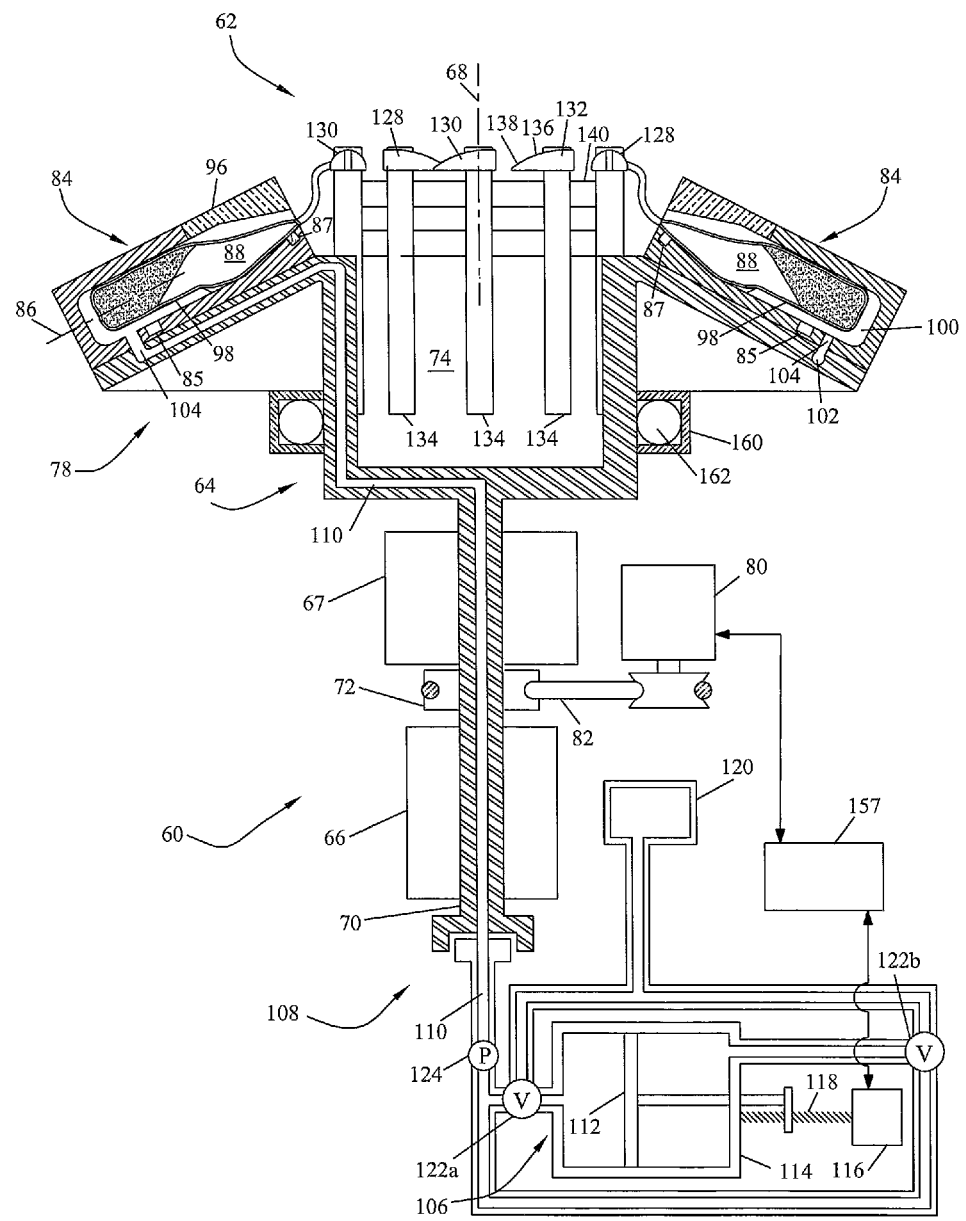
FIG. 2 is a schematic view, partly in cross-section along a diametric plane, of the separation apparatus.

FIG. 2 shows a first embodiment of an apparatus 60 for simultaneously separating by centrifugation four discrete volumes of a composite liquid. The apparatus comprises a centrifuge 62 adapted to receive four of the sets 10 of bags shown in FIG. 1, with the four discrete volumes of a composite liquid contained in the four primary separation bags 12; a component transferring means for transferring at least one separated component from each separation bag into a component bag connected thereto. The apparatus 60 may further comprise means for washing a residual high hematocrit red blood cell component.

The centrifuge 62 comprises a rotor 64 that is supported by a bearing assembly 67 allowing the rotor 64 to rotate around a rotation axis 68. The rotor comprises a cylindrical rotor shaft 70 to which a pulley 72 is connected; a storage means comprising a central cylindrical container 74 for containing component bags, which is connected to the rotor shaft 70 at the upper end thereof so that the longitudinal axis of the rotor shaft 70 and the longitudinal axis of the container 74 coincide with the rotation axis 68. Four identical separation cells 78 are coupled to the central container 74 so as to form a symmetrical arrangement with respect to the rotation axis 68. The centrifuge further comprises a motor 80 coupled to the rotor by a belt 82 engaged in a groove of the pulley 72 so as to rotate the rotor about the rotation axis 68.

Each separation cell 78 comprises a container 84 having the general shape of a rectangular parallelepiped. The separation cells 78 are mounted on the central container 74 so that their respective median longitudinal axes 86 intersect the rotation axis 68, so that they are located substantially at the same distance from the rotation axis 68, and so that the angles between their median longitudinal axes 86 are substantially the same (i.e. 90 degrees). The median axes 86 of the separation cells 78 are inclined downwardly with respect to a plane perpendicular to the rotation axis 68.

Each container 84 comprises a separation cavity 88 that is so shaped and dimensioned as to loosely accommodate a separation bag 12 full of liquid, of the type shown in FIG. 1. The cavity 88 (which will be referred to later also as the "separation compartment") is defined by a bottom wall, which is the farthest to the rotation axis 68, a lower wall that is the closest to the container 74, an upper wall opposite to the lower wall, and two lateral walls. The cavity 88 comprises a main part, extending from the bottom wall, which has substantially the shape of a rectangular parallelepiped with rounded corners and edges, and an upper, or proximal, part, which has substantially the shape of a prism having convergent triangular bases. In other words, the upper part of the cavity 88 is defined by two sets of two opposing walls converging towards the central median axis 86 of the container 84. One interesting feature of this design is that it causes a radial dilatation of a thin layer of a minor component of a composite fluid (e.g. the platelets in whole blood) after separation by centrifugation, and makes the layer more easily detectable in the upper part of a separation bag. This also reduces mixing between component layers by providing a gradual, funnel-like transition into the tube. The two couples of opposite walls of the upper part of the separation cell 78 converge towards three cylindrical parallel channels (not shown), opening at the top of the container 84, and through which, when a separation bag 12 is set in the container 84, the three tubes 18, 20, 22 extend. (Tube 20 along with needle 30 may be removed before the separation bag 12 is placed in the container 84).

The container 84 also comprises a hinged lateral lid 96, which is comprised of an upper portion of the external wall of the container 84. The lid 96 is so dimensioned as to allow, when open, an easy loading of a separation bag 12 full of liquid into the separation cell 78. The container 84 comprises a locking means (not shown) by which the lid 96 can be locked to the remaining part of the container 84. The container 84 also comprises a securing or locating means for securing or locating a separation bag 12 within the separation cell 78. The bag securing or locating means comprises two pins (not shown) protruding on the internal surface of the lid 96, close to the top of separation cell 78, and two corresponding recesses in the upper part of the container 84. The two pins are so spaced apart and dimensioned as to fit into the two holes 24 in the upper corners of a separation bag 12.

The separation apparatus further comprises a component transferring means for transferring at least one separated component from each separation bag into a component bag connected thereto. The component transferring means comprises a squeezing system for squeezing the separation bags 12 within the separation compartments 88 and causing the transfer of separated components into component bags 14, 16. The squeezing system comprises a flexible diaphragm 98 that is secured to each container 84 so as to define an expandable chamber 100 in the cavity thereof. More specifically, the diaphragm 98 is dimensioned so as to line the bottom wall of the cavity 88 and a large portion of the lower wall of the cavity 88. The squeezing system further comprises a peripheral circular manifold 102 that forms a ring. Each expansion chamber 100 is connected to the manifold 102 by a supply channel 104 that extends through the wall of the respective container 84, close to the bottom thereof. The squeezing system further comprises a hydraulic pumping station 106 for pumping a hydraulic liquid in and out of the expandable chambers 100 within the separation cells 78. The hydraulic liquid is selected so as to have a density slightly higher than the density of the densest of the components in the composite liquid to be separated (e.g. the red blood cells, when the composite liquid is blood). As a result, during centrifugation, the hydraulic liquid within the expandable chambers 100, whatever the volume thereof, will generally remain in the most external part of the separation cells 78. The pumping station 106 is connected to the expandable chambers 100, through a rotary seal 108, by a duct 110 that extends through the rotor shaft 70, through the bottom and lateral wall of the central container 74, and, radially outwardly where it connects to the manifold 102. The pumping station 106 comprises a piston pump having a piston 112 movable in a hydraulic cylinder 114 fluidly connected via the rotary seal or fluid coupling 108 to the rotor duct 110. The piston 112 is actuated by a brushless DC motor 116 that moves a lead screw 118 linked to a piston rod. The hydraulic cylinder 114 is also connected to a hydraulic liquid reservoir 120 having an access controlled by two valves 122a, 122b for selectively allowing the introduction or the withdrawal of hydraulic liquid into and from a reciprocating hydraulic circuit including the hydraulic cylinder 114, the rotor duct 110 and the expandable hydraulic chambers 100. A pressure gauge 124 is connected to the hydraulic circuit for measuring the hydraulic pressure therein.

The container 84 further comprises a pressure sensor 85 in the wall of the cavity 88. The pressure sensor 85 has a flexible membrane that moves in response to pressure changes in cavity 88 and such membrane is connected to a pressure transducer to convert such information to pressure information. The pressure sensor 85 senses pressure amount due to the fluid level or head height of fluid in the bag 12. The outboard area of the cavity 88 is from the sensor 85 to the bottom wall or the wall furthest from the rotational axis. The inboard area of the cavity 88 is that area from the sensor 85 to the upper wall of the cavity 88. The container 84 further includes a second optical sensor 87 in the wall of the cavity 88 to detect passage of blood component or interface changes as more fully described below.

The separation apparatus further comprises four sets of three pinch valves 128, 130, 132 that are mounted on the rotor around the opening of the central container 74. Each set of pinch valves 128, 130, 132 faces one separation cell 78, with which it is associated. The pinch valves 128, 130, 132 are designed for selectively blocking or allowing a flow of liquid through a flexible plastic tube, and selectively sealing and cutting a plastic tube. Each pinch valve 128, 130, 132 comprises an elongated cylindrical body 134 and a head 136 having a jaw 138 forming a gap that is defined by a stationary lower plate or anvil 140 and the jaw 138 movable between a "load" position, an "open" position, and a "closed" position. The gap is so dimensioned that one of the tubes 32, 36, 46 of the bag sets shown in FIG. 1 can be snuggly engaged therein when the jaw is in the open position. The elongated body contains a mechanism for moving the jaw and it is connected to a radio frequency generator that supplies the energy necessary for sealing and cutting a plastic tube. It is also noted that a tearable seal could alternatively be used. The pinch valves 128, 130, 132 are mounted inside the central container 74, adjacent the interior surface thereof, so that their longitudinal axes are parallel to the rotation axis 68 and their heads protrude above the rim of the container 74. The position of a set of pinch valves 128, 130, 132 with respect to a separation bag 12 and the tubes 32, 36, 46 connected thereto when the separation bag 12 rests in the separation cell 78 associated with this set of pinch valves 128, 130, 132 is shown in dotted lines in FIG. 1. Electric power is supplied to the pinch valves 128, 130, 132 through a slip ring array 66 that is mounted around a lower portion of the rotor shaft 70.

Figure 3:
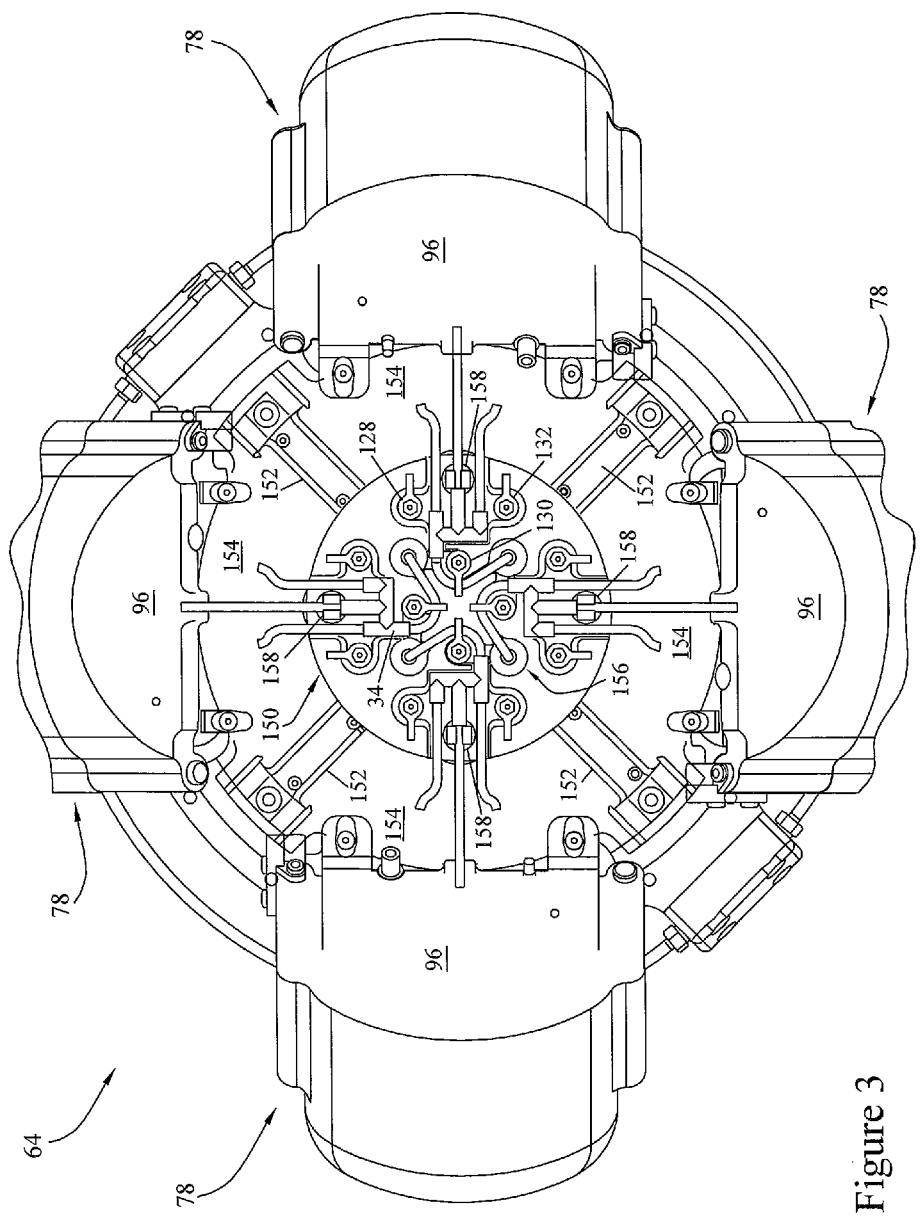
FIG. 3 is a top plan view of the separation apparatus of FIG. 2, showing at least part of a set of bags mounted thereon, along with the separation apparatus valves and sensors.

Rapid placement of tubes, such as tubes 32, 36 and 46, is enhanced by the ability of the valve jaws in the "load" position to optionally swing completely clear of a track or groove adapted to receive a tube. Accurate placement of the tubes is enhanced by the use of the asymmetrical manifold 34. The manifold is comprised of relatively rigid plastic and forms a junction for at least three, preferably four, flexible tubes. Connections for the tubes are asymmetrically spaced around the manifold. As shown in FIGS. 1 and 3 an embodiment of the asymmetrical manifold 34 comprises an "E" configuration. The "E" configuration comprises a central rigid tube 166 with three stubs 168, 171, and 173 connected to tubes 32, 18 and 36, respectively. Diametrically across from the three stubs, a fourth stub 175 connects to tube 46 and thence to the auxiliary bag 44. The fourth stub 175 is asymmetrically placed along the tube 166. Because of the asymmetrical shape of the manifold, the manifold can be mounted in a shaped recess on the central core 150 in only one direction. Each of the tubes 32, 36 and 46 of the bag set 10 will consequently be reliably mounted at the proper valve 128, 130, 132. Although the valve jaws swing in the load position, such movement is optional and it is understood that a manifold, depending on shape, can be loaded without such jaw movement.

The separation apparatus also comprises a controller 157 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. In particular, the microprocessor is programmed for receiving information relative to the centrifugation speed(s) at which the rotor is to be rotated during the various stages of a separation process (e.g. stage of component separation, stage of a plasma component expression, stage of suspension of platelets in a plasma fraction, stage of a platelet component expression, etc), and information relative to the various transfer flow rates at which separated components are to be transferred from the separation bag 12 into the component bags 14, 16. The information relative to the various transfer flow rates can be expressed, for example, as hydraulic liquid flow rates in the hydraulic circuit, or as rotation speeds of the brushless DC motor 116 of the hydraulic pumping station 106. The microprocessor is further programmed for receiving, directly or through the memory, information from the pressure sensor 124 and from the sets of sensors 87 and 158 (described below) and for controlling the centrifuge motor 80, the brushless DC motor 116 of the pumping station 106, and the four sets of pinch valves 128, 130, 132 so as to cause the separation apparatus to operate along a selected separation protocol. The microprocessor also receives information from each pressure sensor 85 and sensors 87 and 158 for volume determination or prediction.

A first balancing means initially balances the rotor when the weights of the four separation bags 12 contained in the separation cells 78 are different. The first balancing means substantially comprises the same structural elements as the elements of the component transferring means described above, namely: four expandable hydraulic chambers 100 interconnected by a peripheral circular manifold 102, and a hydraulic liquid pumping station 106 for pumping hydraulic liquid into the hydraulic chambers 100 through a rotor duct 110, which is connected to the circular manifold 102. Under centrifugation forces, the hydraulic liquid will distribute unevenly in the four separation cells 78 depending on the difference in weight of the separation bags 12 to balance the rotor.

FIG. 3 shows a top plan view of the rotor 64. Four symmetrically spaced separation cells 78 (each with a lid 96) are shown surrounding a central core 150, which contains four sets of valves 128, 130, 132 and which supports the asymmetrical manifolds 34 and tubes of the bag sets 10. The core 150 is supported in the center of the rotor by a spider structure comprised of four radial support arms 152. The arms 152 define collection cavities 154 between a separation cell 78 and an adjacent set of valves 128, 130, 132 on the central core 150. The component bags 14 and 16 (for plasma and platelets respectively) and the red blood cell component bag 38, with its associated filter 40, are placed in the cavity 154 when the bag set 10 is loaded into the rotor 64. The collection and separation bag 12, which initially contains the collected unit of whole blood, is placed in the adjacent separation cell 78. The auxiliary bag 44, which may be used for temporary fluid storage, waste fluid collection or collection of a rare or small-volume blood component, is placed in a well 156 close to the axis of rotation 68 (see FIG. 3) of the rotor. The well 156 is closer to the axis of rotation than at least some of the valves associated with a single set 10 of bags. The well 156 may be cylindrical or rectangular to accommodate a rectangular bag 44, as shown in FIG. 1. The well is positioned such that the processing or primary separation bag 12 is located in a relatively high force region of the centrifugal field produced by the rotation of the rotor, while the component bags 14, 16 are located in a lower force region, and the smaller wash solution or discard bag 44 placed in the well would be in the lowest force region. By reason of bag placement in high, intermediate and low force regions of the centrifugal field, air will tend to collect in the wash bag 44 in the well 156. Moreover, a shorter line or tube can be used to connect the small bag 44 to the entire bag assembly. The three placement zones aid in simplifying the bag assembly and make the process of loading the bag assembly into the rotor easier.

FIG. 3 shows an asymmetric manifold 34 having an "E" configuration (also shown in FIG. 1), although other configurations could be used. For each set of valves, outer valves 128, 132 are shown in "load" configuration, that is, the jaw of the valve does not extend over an adjacent tube, thereby allowing the manifold 34 and tubes to be installed in their proper configuration on the central core 150. For each set of valves, an inner or center valve 130 is shown in the closed position with respect to tube 46.

A tube sensor 158 is able to detect the presence or absence of liquid in the tube 18, such as the detection of plasma, as well as to detect blood cells in a liquid. Each sensor 158 and 87 may comprise a photocell including an infrared LED and a photo-detector. Electric power is supplied to the sensors 87, 158 through the slip ring array that is mounted around the lower portion of the rotor shaft 70. In the process of separating blood into component parts, fluid components, such as plasma or platelets, are expressed out of the separation bag 12 in the separation cell 78 into component bags 14, 16 in the cavities 154. The sensor 158 may detect the beginning of the plasma flow or the presence of platelets or red blood cells. In response, the controller 157 may interrupt or change the processing for the particular set of bags where the new condition was sensed. The second sensor or photocell 87, similar to 158, may also be included in container 84 (see FIG. 2). This sensor 87 is also able to detect the presence or absence of liquid such as plasma as well as the presence of platelets or red blood cells. This sensor may be used to detect the trailing edge of a separated layer or fraction.

Since the process of blood separation proceeds at different rates for different blood units, the volumes and weights of fluids in different bags and locations on the rotor will differ. A second balancing means 160 balances the rotor when the weights of the components transferred into the component bags 14, 16 in the cavities 154 are different. For example, when two blood donations have the same hematocrit and different volumes, the volumes of plasma extracted from each donation are different, and the same is true when two blood donations have the same volume and different hematocrit. The second balancing means comprises a balance assembly or ring 160, more particularly described in U.S. patent application Ser. No. 11/751,748, filed May 22, 2007, and incorporated herein by reference. The balancing apparatus of the separation apparatus comprises one or two balancing assemblies, each including a series of ponderous satellites or balls that can move freely on a specific circular orbit centered on and perpendicular to the axis of rotation of the rotor. The housing comprises a container for spherical ponderous satellites (balls) 162, which are housed in a cylindrical outer race, in which the balls slightly engage, and on which they roll, when the rotor rotates. The balancing means 160 comprises a plurality of balls. When the balls are in contact with each other, they occupy a sector of the ring of about 180 degrees. The balancing means 160 also comprises a damper or dampening fluid or element for providing resistance to the movement of the balls.

The method of using the apparatus described above will now be described.

Each procedure to separate composite fluid or whole blood begins with collection of the whole blood or fluid into bag 12 of bag set 10. The bag set 10 is then loaded onto apparatus 60. Before loading the bag set 10, needle 30 and tube 20 may be removed by sterile welding or other procedure. The bag 12 containing the composite fluid or whole blood is placed in the cavity 88. This may be done for each cavity 88 of the apparatus 60. The collection bags and other fluid bag, if any, is placed in the respective cavity 154 or 156. The rotation of the rotor 64 begins and the rotor 64 is rotated until it reaches an rpm suitable for separation, (for example 1800 to 3200 rpm). A pressure sensing value at a designated rpm is provided by pressure sensor 85 to the control unit 157. Pressure sensor 85 senses the fluid pressure in the cavity 88 due to the head height or fluid level of the composite fluid. The valves may be opened or closed during the pressure sensing step. Pressure may be determined also after loading of bag 12 but before the rotor 64 begins its rotation. The fluid pressure measurement is used by the controller to predict the volume of the composite fluid or whole blood. The pressure amount corresponds to the fluid level or head height and thus corresponds to the composite fluid volume.

During centrifugation, fluid in the separation bag 12 is subject to a radial acceleration gradient. This causes a pressure gradient along a radial line passing through the fluid volume. The resulting pressure depends on the angular velocity, radius and fluid density.

Pressure sensor 85 measures the fluid pressure at a known radial location in the separation bag 12. The rotor speed or rpm of the rotor 64 is known as is the radial location of the pressure sensor 85 on the centrifuge 62. The sensor 85 is further located at a specific location along the wall of the separation compartment 88. A portion of the composite liquid will be outboard or between the sensor 85 and the bottom of the separation compartment 88. The volume of composite fluid can be determined from the volume of the outboard area containing such fluid. Fluid variations may occur in the inboard area of the separation compartment due to the overall volume of the composite fluid. Larger volumes of fluid cause more fluid to be located in the inboard area or the area between the sensor 85 and the top of the separation compartment. As fluid volume increases inboard of the pressure sensor 85 the magnitude of the pressure at the sensor 85 location also increases. The radial distance from the fluid surface to the pressure sensor location can be determined. The volume of the outboard area is known from the separation compartment 88 geometry and the volume of the inboard area can be estimated by variations in pressure due to the pressure sensor 85. Adding the outboard volume to the inboard volume provides an estimate or prediction of the total volume of the composite fluid.

As rotation continues, valve 128 opens or remains opens and plasma, the least dense component in whole blood, flows into bag 14. The hydraulic fluid from reservoir 120 flows through duct 110 and channel 104 and under bladder or diaphragm 98 to squeeze bag 12 to facilitate plasma transfer to bag 14. Photocell 158 optically sees the leading edge of the plasma flow and provides such information to controller 157. When photocell or sensor 57 senses a cellular component approaching tubing 18 from the top of bag 12, it also provides the information including the trailing edge of the plasma interface to the controller 157. The controller sends a signal to close valve 128 and open valve 132 for cellular component. The hydraulic flow rate corresponds to the fluid flow rate into the collection bag 14 and 16. From this flow rate and the sensor signals 57, 158 determining the start (leading edge) and end (trailing edge) of the plasma collection, the volume of plasma or an expressed component can be determined.

Sensors 57 and 158 further can sense the change of cellular component from, for example, platelets to red blood cells. Photocell 158 indicates the leading edge of the platelet layer with photocell 57 indicating the trailing edge. This sensing of an interface change between different layers or sedimented blood components will cause the controller to signal valve 132 to close and end the platelet collection. The leading edge sensor 158 signal indicating platelets along with the trailing edge sensor 57 signal indicating the end of the platelet layer is provided to the controller, along with the fluid flow rate, to determine or estimate the volume of platelets transferred. The estimated plasma volume as well as the determined platelet volume along with the initial whole blood volume estimate can be used by the controller to provide an estimate of the remaining component or components such as red blood cells in bag 12.

If it is desired to add wash solution or storage solution into the remaining red blood cells, the hydraulics 112 may be pulled back to drain out from under diaphragm or membrane 98 to release the squeezing pressure on the previously squeezed bag 12. Valve 130 may be opened and wash or storage solution may be introduced from bag 44 through tubing 46 to bag 12.

If washing is the desired protocol, the wash solution may be mixed with the red blood cells and resulting supernatant can be expressed back to bag 44 using the hydraulic fluid to squeeze bag 12 for the transfer.

If the storage solution is added from bag 44, the centrifuge will be stopped. The bag set 10 may be removed from the centrifuge and all tubing but 22 can be discarded.

Storage solution can be also gravity drained from bag 38 through filter 40 to mix with remaining red blood cells in bag 12.

Valves 128, 130 and 132 can provide heat sealing of the tubing 32, 46 and 36. Any remaining tubing can also be heat sealed by the operator for removal leaving bag 12, tubing 22, filter 40 and bag 38 remaining. The residual product, such as red blood cells and storage solution, is drained from bag 12 to 42. Frangibles 28 and 42 are opened and bag 12, is elevated to gravity drain the red blood cells through leukoreduction filter 40 to bag 38.

The above procedure is only exemplary to describe the invention as it is understood that variations can occur. Although sensors 57 and 58 are described, it is understood that sensor 158 or sensor 57 only may be used to detect both a leading or trailing edge or interface change. Also, additional optical sensors may be provided around container 84 similar to sensor 57 to detect fluid or cells. Also, white blood cells may also be collected.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method of predicting the volume of a component separated from whole blood, the method comprising:
   sensing, at a known radial location, a fluid pressure in a separation cavity containing whole blood using a pressure sensor in a wall of the separation cavity, the pressure sensor comprising a flexible membrane that moves in response to pressure changes in the cavity and such membrane being connected to a pressure transducer;
   predicting the volume of the whole blood from the sensing the fluid pressure step and an outboard volume located between the sensor and the bottom of the separation cavity;
   separating the whole blood into at least a first and second component;
   expressing the first separated component from the separation cavity to a collection cavity using an expandable chamber in the separation cavity, the expandable chamber being connected to a hydraulic circuit, wherein a pressure gauge is connected to the hydraulic circuit for measuring hydraulic pressure therein;
   sensing the movement of the first separated component;
   determining the volume of the expressed first separated component from the sensing the movement step; and
   predicting the volume of the second component remaining in the separation cavity from the predicted volume of the whole blood and the determined volume of the expressed first separated component.

2. The method of claim 1 wherein the sensing the movement of the first separated component comprises:
   sensing the leading edge of the expressed first component by detecting the presence of fluid; and
   sensing the trailing edge of the expressed first component by detecting the presence of components not in the first expressed component.

3. The method of claim 2 wherein the step of sensing the leading edge comprises optically sensing the leading edge with a photocell.

4. The method of claim 2 wherein the step of sensing the trailing edge comprises optically sensing the trailing edge with a photocell.

5. The method of claim 3 wherein the step of sensing the leading edge comprises locating the photocell to detect fluid in tubing between the separation cavity and the collection cavity.

6. The method of claim 4 wherein the step of sensing the trailing edge comprises locating the photocell near the exit of the separation cavity.

7. The method of claim 1 wherein the separating step comprises centrifugally separating the whole blood.

8. The method of claim 1 wherein the separating further comprises separating the whole blood into at least a first, second and third component, and the method further comprises:
   expressing the third separated component from the separation cavity to the collection cavity after the step of expressing the first separated component;
   sensing the movement of the third separated component;
   determining the volume of the expressed third separated component from the sensing the movement of the third separated component step;
   predicting the volume of the second component remaining in the separation cavity from the predicted volume of the whole blood, the predicted volume of the expressed first component and the predicted volume of the expressed third component.

9. The method of claim 8 wherein, the first component is plasma, the third component is platelets and the second component is red blood cells.

10. The method of claim 1 wherein the first component is plasma and the second component is red blood cells.

11. The method of claim 9 wherein the sensing the movement of the first separated component comprises:
   sensing the leading edge of the plasma by detecting the presence of the plasma; and
   sensing the trailing edge of the plasma by detecting the presence of platelets.

12. The method of claim 11 wherein the sensing the movement of the third separated component comprises:
   sensing the leading edge of the platelets by detecting the presence of the platelets; and
   sensing the trailing edge of the platelets by detecting the presence of red blood cells.

13. The method of claim 9 wherein the sensing the movement of the first separated component comprises:
   sensing the leading edge of the plasma by detecting the presence of the plasma; and
   sensing the trailing edge of the plasma by detecting the presence of a cellular component.

14. The method of claim 1 wherein the step of sensing the fluid pressure comprises:
   sensing, with the pressure sensor, the fluid pressure in a separation bag containing the whole blood; and
   the step of expressing the separated first component comprises expressing the first component from the separation bag in the separation cavity to a bag in the collection cavity.

15. The method of claim 8 wherein the step of sensing the fluid pressure comprises:
   sensing, with the pressure sensor, the fluid pressure in a separation bag in the separation cavity; and
   the step of expressing the separated first component comprises expressing the first component from the separation bag in the separation cavity to a first bag in the collection cavity; and
   the step of expressing the separated third component comprises expressing the third component from the separation bag in the separation cavity to a second bag in the collection cavity.

16. The method of claim 15 wherein the expressing steps comprise:
   squeezing, with the expandable chamber, the separation bag to transfer the first component to the first bag and to transfer the third component to the second bag.

* * * * *